(12) United States Patent
Capra et al.

(10) Patent No.: US 11,786,862 B2
(45) Date of Patent: Oct. 17, 2023

(54) PLANT AND METHOD FOR THE SEPARATION OF A GAS MIXTURE CONTAINING A PLURALITY OF COMPONENTS, IN PARTICULAR FOR OBTAINING BIOMETHANE

(71) Applicant: AB IMPIANTI SRL, Orzinuovi (IT)

(72) Inventors: Federico Capra, Soragna (IT); Stefania Patronelli, Taranto (IT); Egidio Monticelli, Brescia (IT)

(73) Assignee: AB IMPIANTI SRL, Orzinuovi (IT)

( * ) Notice: Subject to any disclaimer, the term of this patent is extended or adjusted under 35 U.S.C. 154(b) by 314 days.

(21) Appl. No.: 17/108,360

(22) Filed: Dec. 1, 2020

(65) Prior Publication Data

US 2021/0170329 A1 Jun. 10, 2021

(30) Foreign Application Priority Data

Dec. 4, 2019 (IT) .......................... 102019000022983

(51) Int. Cl.
| | | |
|---|---|---|
| *B01D 53/22* | (2006.01) | |
| *B01D 53/047* | (2006.01) | |
| *C07C 7/00* | (2006.01) | |
| *C07C 7/12* | (2006.01) | |
| *C07C 7/144* | (2006.01) | |
| *C10L 3/10* | (2006.01) | |

(52) U.S. Cl.
CPC ....... *B01D 53/229* (2013.01); *B01D 53/0476* (2013.01); *B01D 53/226* (2013.01); *C07C 7/005* (2013.01); *C07C 7/12* (2013.01); *C07C 7/144* (2013.01); *C10L 3/104* (2013.01); *B01D 2256/245* (2013.01); *B01D 2257/504* (2013.01); *C10L 2290/542* (2013.01); *C10L 2290/548* (2013.01)

(58) Field of Classification Search
None
See application file for complete search history.

(56) References Cited

U.S. PATENT DOCUMENTS

| | | | | |
|---|---|---|---|---|
| 4,690,695 | A | * 9/1987 | Doshi | ................... B01D 53/229 95/55 |
| 4,783,203 | A | * 11/1988 | Doshi | ................... B01D 53/229 95/143 |
| 5,411,721 | A | 5/1995 | Doshi et al. | |

(Continued)

FOREIGN PATENT DOCUMENTS

EP 0 241 313 10/1987

OTHER PUBLICATIONS

Search Report for IT 102019000022983 dated Jul. 17, 2020, 10 pages.

*Primary Examiner* — Jason M Greene
(74) *Attorney, Agent, or Firm* — NIXON & VANDERHYE

(57) ABSTRACT

Plant and method for the separation of a gas mixture containing a plurality of gaseous components, comprising first and second membrane-based separation stages and a third gas separation stage with adsorption with oscillating pressure, the first, second and third gas separation stages acting in combination to obtain a first final flow of gas enriched in a first component of the initial gas mixture, for example methane, and a second final flow of gas, enriched in a second component of the initial gas mixture, for example carbon dioxide.

11 Claims, 6 Drawing Sheets

(56) References Cited

U.S. PATENT DOCUMENTS

| | | |
|---|---|---|
| 2012/0085232 A1 | 4/2012 | Sethna et al. |
| 2013/0108531 A1* | 5/2013 | Mitariten ............. B01D 53/229 |
| | | 95/138 |
| 2016/0229771 A1 | 8/2016 | Paget et al. |
| 2017/0320736 A1* | 11/2017 | Voss ..................... B01D 53/229 |
| 2018/0112142 A1* | 4/2018 | Foody ................... B01D 53/22 |
| 2019/0126187 A1* | 5/2019 | Tanaka ................. B01D 53/229 |
| 2022/0259512 A1* | 8/2022 | Keller .................. B01D 53/229 |

* cited by examiner

PLANT AND METHOD FOR THE SEPARATION OF A GAS MIXTURE CONTAINING A PLURALITY OF COMPONENTS, IN PARTICULAR FOR OBTAINING BIOMETHANE

The present disclosure relates in general to a plant and a method for the separation of a gas mixture containing a plurality of gaseous components, and more in particular for the separation of a gas mixture into at least a first final flow of gas enriched in a first component and into a second final flow of gas enriched in a second component of said plurality of components.

In particular, the plant and the method according to the disclosure are especially suitable to be used with an initial mixture of biogas in order to extract a first flow enriched in methane or bio-methane ($CH_4$), and a second flow enriched in carbon dioxide ($CO_2$), and they will be described hereinafter with reference to this specific application without intending however to limit in any way their application to other types of gas mixtures for the extraction of flows enriched in gases other than the ones mentioned above.

As is known, in the energy sector, over the course of the last decades, the attention to research, development and sustainable exploitation of energy resources alternative to traditional ones has grown significantly, at the same time paying great attention to all aspects linked to environmental impact and eco-sustainability.

To this end, various technological trends have been explored and, among these, diverse technologies have been developed aimed at exploiting gas masses of natural origin, the so-called biogas, resulting for example from fermentation of animal sewage, from waste or material of vegetal origin, from landfills, from wastewater treatment, etc.

These technologies are mainly based on the use of special membranes which make it possible to selectively separate the gas mixtures into various components and they are used in plants having several separation stages, according to multiple operational configurations which vary depending on the type of initial mixture to be treated and, above all, on the final result to be obtained.

In fact, the plant configuration for a given gas mixture and successive separation into the component or components desired, depends on numerous factors, such as: the type of final product to be extracted; the acceptable percentage of purity of the desired product and the commercial value of said product; the number of stages and machinery necessary to realize the plant as a whole.

In particular, one of the parameters which has the most impact on the choice of design is given by the cost of the membranes and by that of the compression means associated with the various separation stages and which are necessary to guarantee an adequate efficiency of the membranes; in fact, the result of the separation which can be obtained by means of the membranes in a separation stage depends not only on the characteristics of the membranes but also on the pressure ratio between the high pressure and low pressure sides of the membrane itself. The higher the pressure ratio, the better is the result of the maximum separation achievable.

Therefore, one of the drawbacks of the solutions of the known art is that, in order to obtain an adequate purity of the desired gas, it is necessary to use a plurality of stages and a plurality of separate compressors driven by corresponding engines which increase the complexity and the costs for the realization, operation and maintenance of the plants. Alternatively, it is necessary to increase the overall working surface of the membranes thus, in practice, increasing the number of membranes to be used, whose cost per unit is notoriously high.

In any case, in plants with multiple stages, for example with three or more membrane-based gas separation stages, after having gone through the initial separation stages, typically two, the gas mixture may still contain a significant percentage of the component which has to be extracted and, therefore, is then treated by means of one or more further membrane separation stages.

In this case, even though the quantity of residual gas to be extracted is still considerable, the cost of carrying out and operating the additional one or more stages is negatively disproportionate to the additional quantity of gas which can be extracted.

It follows that, where the plants use these additional stages, the overall cost-benefit ratio is reduced; on the contrary, not using said additional stages reduces the quantity and the quality of the final desired result, with emission into the atmosphere of some of the gas having environmental impact.

Therefore, despite the fact that the solutions available on the market today make it possible to obtain fairly good results, it is clear from what has been pointed out above that it is still necessary to find new solutions which allow a further improvement compared to the present state of the art.

To this end, there is provided a plant for the separation of a gas mixture containing a plurality of gaseous components, comprising:
- a first membranes-based gas separation stage, adapted to receive in input a flow of said gas mixture and to separate it in a first flow of retentate gas, initially enriched in a first component of said plurality of components, and in a first flow of permeate gas, initially enriched in a second component of said plurality of components;
- a second membranes-based gas separation stage adapted to receive in input said first flow of retentate gas and to separate it into a final flow of retentate gas further enriched in said first component and in a second flow of permeate gas suitable to be recirculated in the plant upstream of said first membranes-based gas separation stage;
- a third gas separation stage with adsorption with oscillating pressure, said third gas separation stage being adapted to receive said first flow of permeate gas in input and to separate it, by means of adsorption, in a recirculable gas flow suitable to be recirculated in the plant upstream of said first membranes-based gas separation stage and in a final gas flow further enriched in said second component.

The present disclosure also provides a method for the separation of a gas mixture containing a plurality of gaseous components, comprising:
- separating, by means of a first membranes-based gas separation stage, a flow of the gas mixture entering the plant, in a first flow of retentate gas, initially enriched in a first component of said plurality of components, and in a first flow of permeate gas initially enriched in a second component of said plurality of components;
- separating, by means of a second membranes-based gas separation stage, said first flow of retentate gas into a final flow of retentate gas further enriched in said first component and in a second flow of permeate gas suitable to be recirculated in the plant upstream of the first membranes-based gas separation stage;

separating, by means of a third gas separation stage with adsorption with oscillating pressure, said first flow of permeate gas initially enriched in a second component of said plurality of components, in a recirculable gas flow suitable to be recirculated in the plant upstream of said first membranes-based gas separation stage and in a final gas flow further enriched in said second component.

Further characteristics and advantages of the present disclosure will become more apparent from the following detailed description of an exemplary but non-limiting embodiment thereof, as illustrated in the accompanying drawings, in which.

Figure 1:
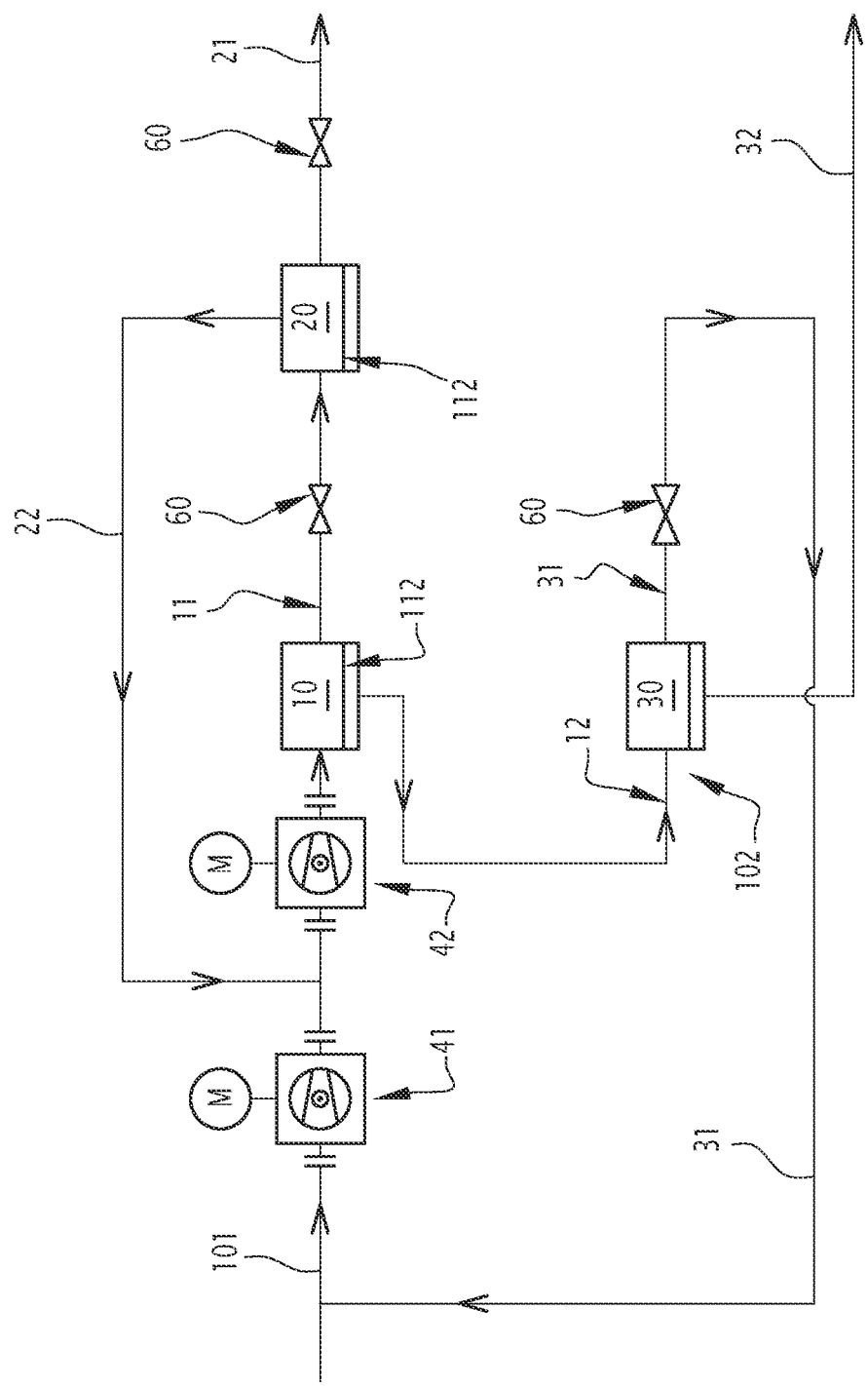
FIG. 1 is a block diagram schematically showing an embodiment of a plant for the separation of a gas mixture according to the present disclosure.
Figure 2:
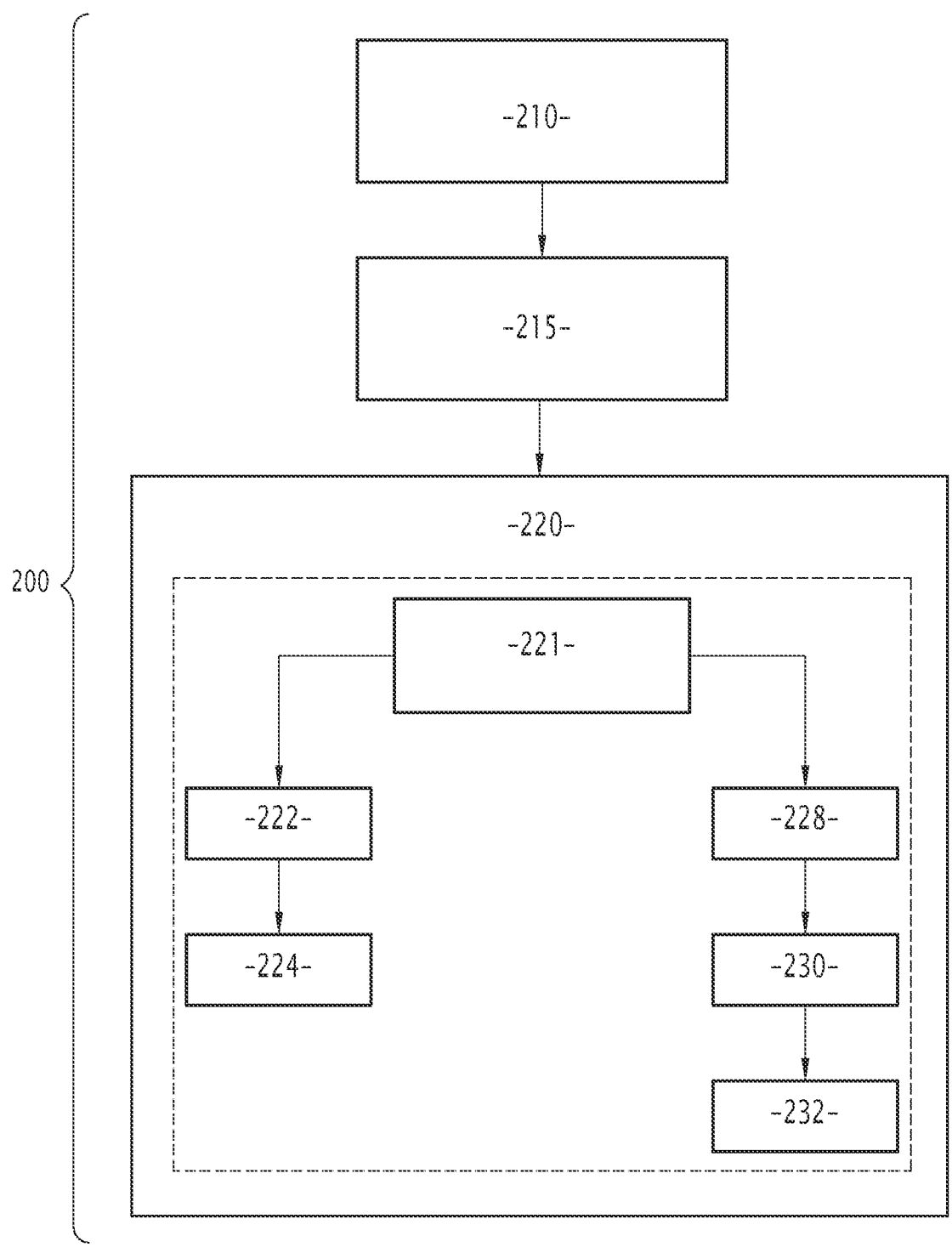
FIG. 2 is a flow diagram schematically showing a method for the separation of a gas mixture according to the present disclosure.
Figure 3:
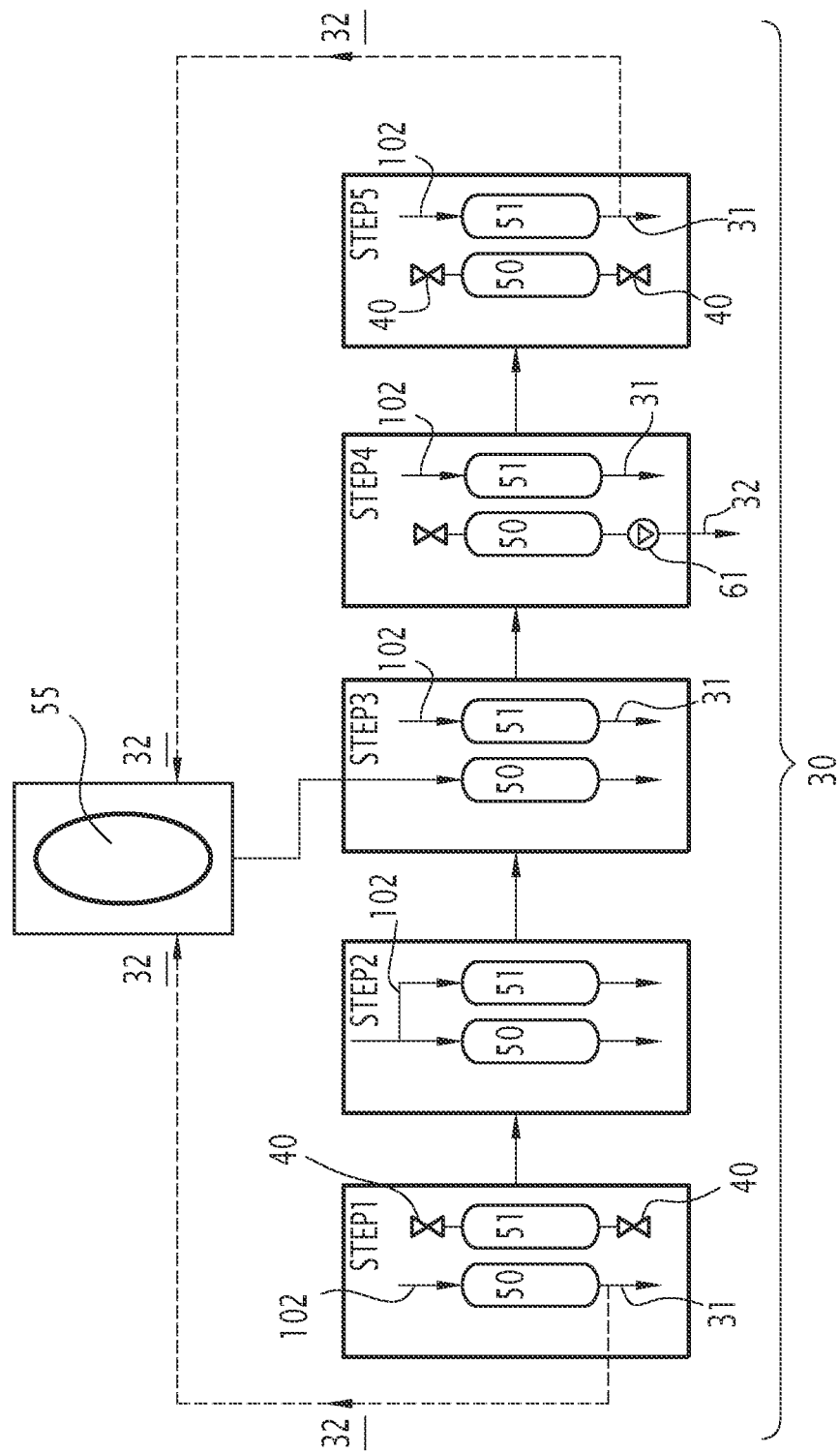
Figure 4:
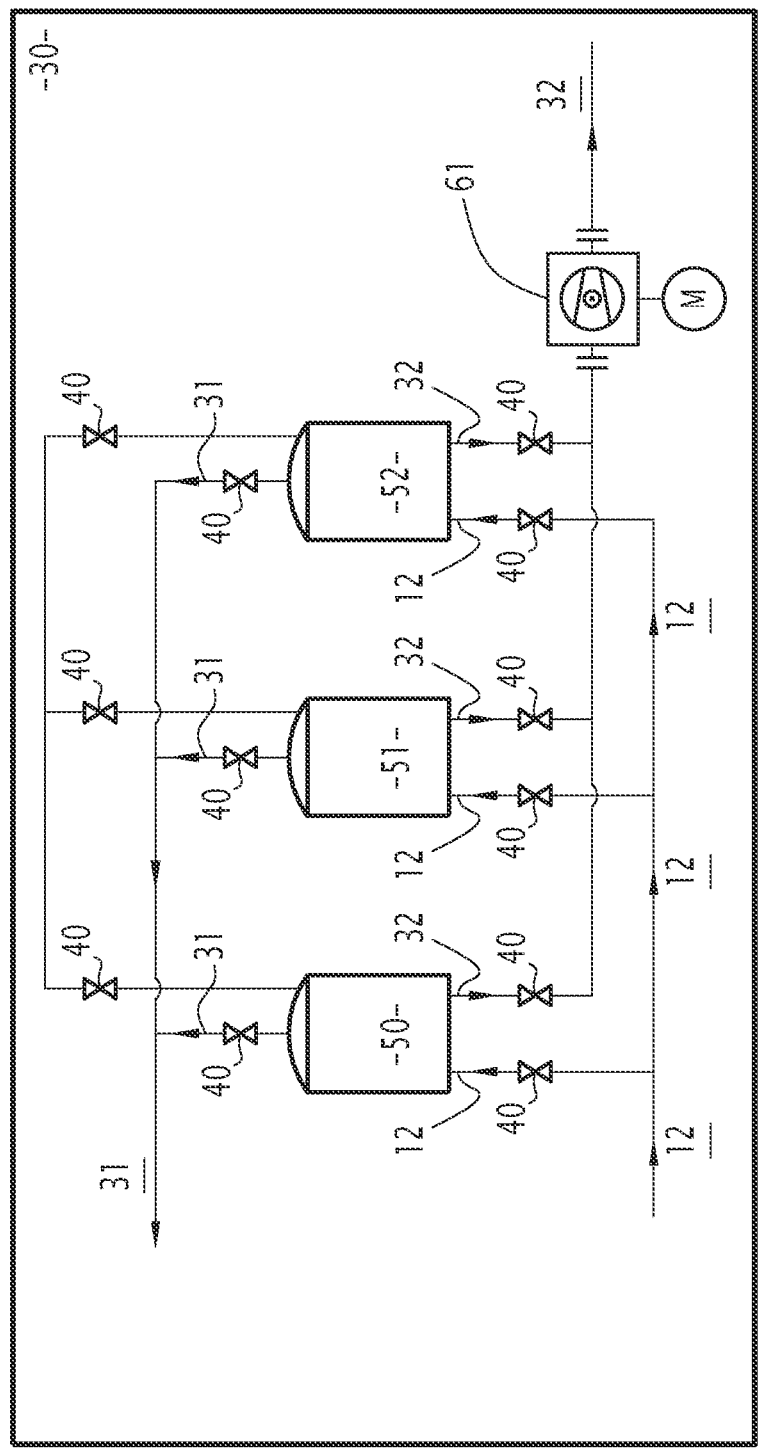
Figure 5:
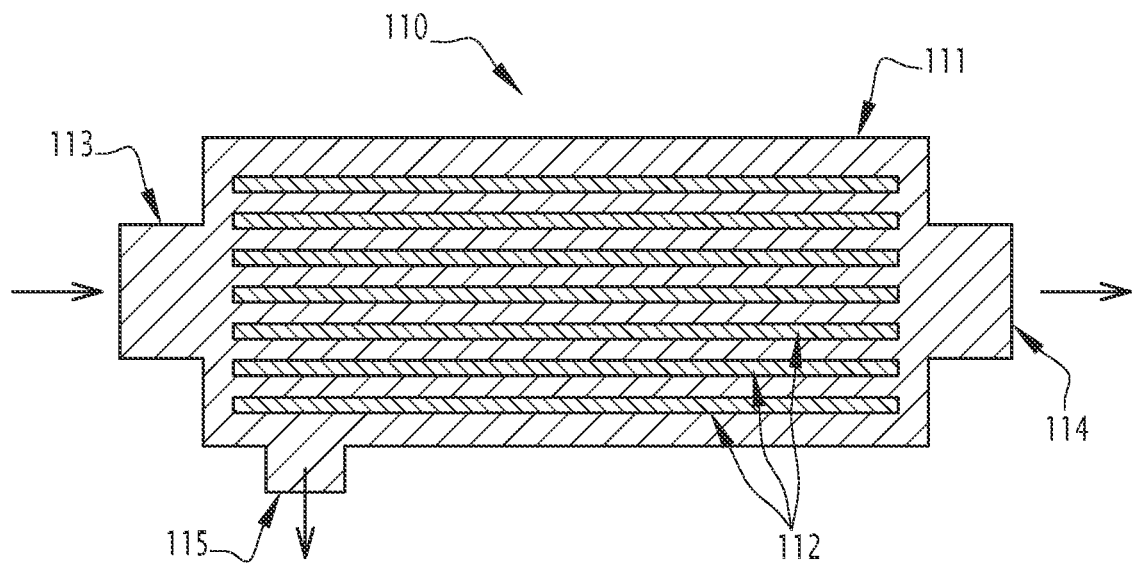
Figure 6:
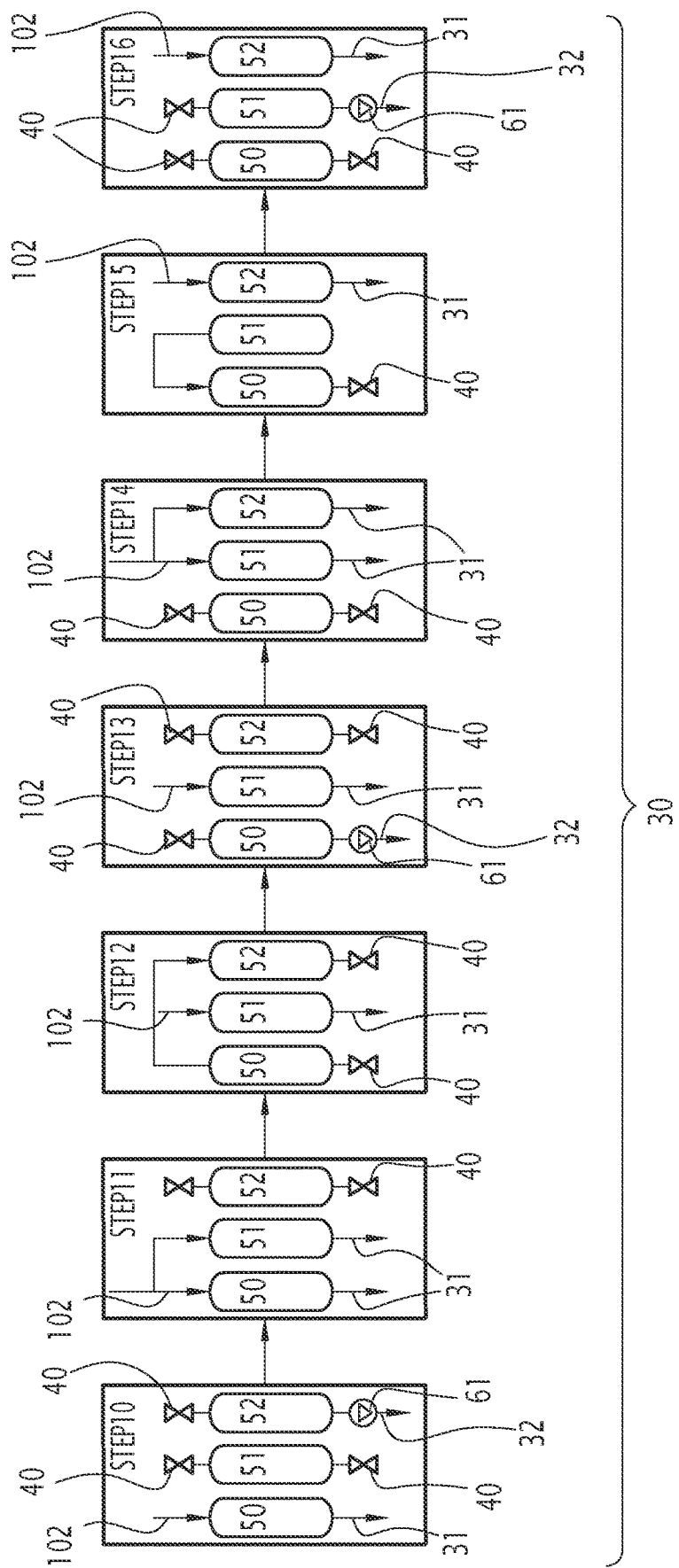

FIG. 3 schematically shows an operating sequence relative to a first embodiment of a gas separation stage with adsorption with oscillating pressure to be used in the plant of FIG. 1 and to carry out the method of FIG. 2;

FIG. 4 schematically shows a second embodiment of a gas separation stage with adsorption with oscillating pressure to be used in the plant of FIG. 1 and to carry out the method of FIG. 2;

FIG. 5 schematically shows an example of a membrane-based gas separation module to be used in the plant of FIG. 1 and to carry out the method of FIG. 2;

FIG. 6 schematically shows an operating sequence relative to the second embodiment of a gas separation stage with adsorption shown in FIG. 4.

It should be noted that in the following detailed description, identical or similar components, from both structural and/or functional points of view, may be indicated with the same reference numbers, independently from the fact that they are shown in different embodiments or in different components of the present description; furthermore, it should be noted that, in order to illustrate this description clearly and concisely, the drawings are not necessarily to scale and certain characteristics of the description may be shown in a rather schematic form.

Furthermore, when the term "adapted" or "configured" or "shaped", or similar, is used in this context with reference to any component whatsoever as a whole or to any part whatsoever of a component, it must be understood as comprising correspondingly the structure and/or configuration and/or the shape and/or the positioning of the component or part to which it refers. In particular, when said terms refer to hardware or software electronic means, they are to be understood as including circuits or parts of electric circuits, as well as software/firmware, for example algorithms, routines and programs in general, under execution in and/or resident in any given storage medium whatsoever.

FIG. 1 schematically shows an embodiment of a plant 100 for the separation of an initial gas mixture 101 containing a plurality of gaseous components according to the present disclosure.

In particular, the plant 100 is configured to separate the gas mixture 101 into at least a first final flow of gas enriched in a first gaseous component (A) and into a second final flow of gas enriched in a second gaseous component (B), forming part of the plurality of components of the mixture 101.

According to a preferred but non-limiting embodiment, the initial gas mixture 101 is made up of a mixture of biogas resulting for example from fermentation of animal sewage and may comprise mainly and in varying quantities methane ($CH_4$), carbon dioxide ($CO_2$), ammonia ($NH_3$), hydrogen sulfide ($H_2S$), water ($H_2O$), nitrogen ($N_2$), oxygen ($O_2$); other substances may be present in smaller and variable quantities. These gas mixtures, before entering the supply line, for example by means of a blower 41, can be subjected to pre-treatment, for example in scrubbers, according to embodiments well known to persons skilled in the art and, for this reason, not described in detail herein.

In this case, the plant 100 is advantageously configured in such a way that the final gas flow further enriched in the first component (A) is a flow of gas enriched in bio-methane ($CH_4$), and the final gas flow further enriched in the second component (B), is a flow of gas enriched in carbon dioxide ($CO_2$).

As shown in FIG. 1, the plant 100 comprises at least:
a first membrane-based gas separation stage 10;
a second membrane-based gas separation stage 20; and advantageously
a third gas separation stage 30 with adsorption with variable or oscillating pressure, indicated with the international terminology "Pressure Swing Adsorption".

According to a particularly preferred embodiment, and according to the modalities described in greater detail in the following description, the third gas separation stage (30) is of the type with adsorption with regeneration at sub-atmospheric pressure, indicated with the international terminology Vacuum Swing Adsorption (VSA), or Vacuum Pressure Swing Adsorption (VPSA).

In a possible embodiment, the first membrane-based gas separation stage 10, and the second membrane-based gas separation stage 20, each comprise at least a module 110, preferably a plurality of modules 110 connected in parallel to each other and an exemplary embodiment of which is schematically shown in FIG. 5.

In particular, each module 110 comprises a casing 111 which contains one or, more preferably, multiple hollow polymeric fibers 112; the casing 111 is provided with a gas inlet port 113 for the intake of the gas flow entering into the corresponding separation stage, with a first gas outlet port 114 and with a second gas outlet port 115, to allow the outflow of flows of retentate or permeate gases, obtained as a result of the interaction between the gas introduced and the membrane or membranes of the stage itself.

For example, the membranes can be of the type CO-810FSC or CO-810FC or CC-1610NFH or CC-1610SEH, marketed by the company UBE Europe GmbH.

As illustrated in FIG. 1, upstream of the first membrane-based gas separation stage 10, besides the blower 41, a compressor 42 is provided to bring the pressure of the flow of the gas mixture 101 to be treated to an adequate pressure when entering the first separation stage 10, for example between 9 and 10 barg.

Therefore, the first membrane-based gas separation stage 10 receives the compressed flow of gas mixture coming out of the compressor 42 and is configured to separate it into a first flow of retentate or not permeate gas 11, initially enriched in the first component (A), and into a first permeate gas flow 12 initially enriched in the second component (B).

As illustrated in FIG. 1, the second membrane-based gas separation stage 20 is positioned downstream of the first membrane-based gas separation stage 10, for example near the first gas outlet port 114, and is suitable to receive the first incoming retentate gas flow 11, initially enriched in said first component (A), and to separate it again into a final retentate gas flow 21 further enriched in said first component (A) and into a second permeate gas flow 22.

The final flow of retentate gas 21, further enriched in said first component (A), comprises for example between 95% and 98% of methane gas ($CH_4$).

In this case, therefore, bio-methane is obtained having adequate purity which can be used as an energy source, introducing it, for example, into a methane gas distribution network, so avoiding its emission into the environment and preventing at the same time its negative greenhouse effect.

The second flow of permeate gas 22, which may contain percentages of the gaseous component (A) more or less significant, can be further recycled, for example by pre-circulating it towards the area upstream of the first separation stage 10.

For example, the second flow of permeate gas 22 is re-circulated upstream of the compressor 42 where it can be added to a new flow of gas mixture 101 coming out of the blower 41 and be treated again together with said new flow, exactly as described above. Advantageously, in the plant 100 according to the present disclosure, the first flow of permeate gas 12, initially enriched in said second component (B), is sent directly, without subjecting it to a further compression, to the third gas separation stage 30, positioned downstream of the first separation stage 10 for example near the second gas outlet port 115.

In its turn, the third gas separation stage 30 with adsorption with oscillating pressure, is configured to receive in input the first flow of permeate gas 12 from the first separation stage 10 and to separate it, by means of adsorption, into a flow of recirculable gas 31 suitable to be re-circulated in the plant upstream of the first membrane-based gas separation stage 10, and into a final gas flow 32 further enriched in the second component (B).

In particular, the further flow of recirculable gas 31, which may still contain more or less significant percentages of the gaseous component (A) and/or of the gaseous component (B), is recirculated directly upstream or downstream of the blower 41, depending on the pressure made available by the separation stage 30, where a new flow of gas mixture 101 can be added and treated again together with it, exactly as described above.

In the plant 100 according to the disclosure, the third gas separation stage 30 comprises a plurality of separation tanks, i.e. two or more tanks, suitable to be connected to a supply line of the first flow of permeate gas 12 and each containing adsorbing means 1 for the separation, by means of adsorption, of the first flow of permeate gas 12 into said flow of re-circulable gas 31 and into said final gas flow 32 further enriched in said second component (B).

As will be seen in the following detailed description, according to the embodiment shown in FIG. 3 there are foreseen two separation tanks 50 and 51, while according to the embodiment shown in FIGS. 4 and 6 there are foreseen three separation tanks 50, 51, 52.

The adsorbing means 1, depending on the gas mixture to be treated and above all on the final components (A) and/or (B) to be obtained, can be composed of one or more adsorbing filters, for example filters made of beds of molecular sieves, such as zeolites and aluminophosphates, silica gel, alumina, resins and/or polymers.

In particular, the tanks of the plurality of separation tanks 50,51,52 are operatively connected to each other and to the various supply lines of the plant 100, by means of one or more valves schematically shown in the various figures by the reference number 40, so that during operation of the plant 100, under steady state operational conditions, they are switched in rotation among them with:

at least a first tank 50 of the plurality of separation tanks isolated from the supply line of the first flow of permeate gas 12, i.e. where the flow inside the first tank 50 is temporarily interrupted, and is subjected to a regeneration phase of the adsorbing means 1 contained therein by applying inside the first tank 50 a first pressure, preferably lower than the atmospheric pressure by operating a vacuum pump 61; and, at the same time:

at least one of the remaining separation tanks 51, 52 is connected to the supply line and continues to be fed, at a second pressure higher than said first pressure, for example between 0.3 and 1 barg, with the first flow of permeate gas 12, continuing the separation process in order to generate the flow of re-circulable gas 31 and the final gas flow 32 further enriched in the second component (B).

In this way, in rotation, while the adsorbing means 1 of at least one tank saturated during the previous adsorbing phases are regenerated, operation of the plant 100 and production of gases enriched in components (A) and (B) continue thanks to one or more of the remaining tanks which remain operative on-line.

According to a first possible embodiment of the plant 100 of the disclosure shown in FIG. 3, the third gas separation stage 30 comprises a first separation tank 50 and a second separation tank 51 containing respective adsorbing means 1 dedicated to the separation of the first flow of permeate gas 12; furthermore, a storage tank 55 is provided connected to said first and second separation tanks 50 and 51 for the storage of at least a part of the final gas flow 32 further enriched in said second component (B), for example carbon dioxide ($CO_2$).

In particular, according to this first embodiment, a part of the final gas flow 32 produced by the separation tanks 50 and 51 is stored in the storage tank 55 and is destined to be subsequently re-introduced inside the first and the second separation tanks for washing the adsorbing means 1 contained therein during the respective regeneration phase.

In a second possible embodiment, as schematically shown in FIG. 4, the third gas separation stage 30 comprises a first separation tank 50, a second separation tank 51 and a third separation tank 52, operatively connected to each other and to various plant supply lines by means of one or more valves 40, so that during operation of the plant 100, in particular under steady state operational conditions, they are switched in rotation among them with:

at least a first tank of the plurality of separation tanks, for example initially the first tank 50, isolated from the supply line of the first flow of permeate gas 12, i.e. where said flow inside the first tank 50 is temporarily interrupted, and is subjected to a regeneration phase of the adsorbing means 1 contained therein by applying inside the first tank 50 a first pressure, preferably lower than the atmospheric pressure by operating a vacuum pump 61; and at the same time a second tank of the plurality of separation tanks, for example the tank 51, which remains connected to the supply line and continues to be fed, at a second pressure higher than said first pressure, for example between 0.3 and 1 barg, with the first flow of permeate gas 12, continuing the separation process in order to generate the flow of recirculable gas 31 and the final flow of gas 32 further enriched in the second component (B);

and the third separation tank, for example the third tank 52, having finished the regeneration phase of its adsorbing means 1 and still isolated from the supply line 102 of the first flow of permeate gas 12 and waiting to be reconnected thereto.

In particular, in this second embodiment, reconnection of the third separation tank 52 to the supply line 102 of the first flow of permeate gas 12 takes place by connecting simultaneously the flow of permeate gas 12 to the third separation tank 52 and to the second separation tank 51, so that the flows of gas which pass through the second tank 51 are at least partially deviated also inside the third tank 52.

When the adsorbing means contained in the second tank 51 have reached the saturation point, the third tank 52 replaces the second tank 51 for production of the flow 31 while the second tank 51 is isolated from the supply line 102. Afterwards, the first tank 50, which meanwhile has been regenerated, is connected to the second separation tank 51 in order to temporarily equalize the pressure inside the first tank 50 with that inside the second tank 51 at a pressure level intermediate between the first pressure and the second pressure.

Once this pressure equalization has taken place, the first tank 50 remains isolated and waits to be reconnected to the supply line 102 in order to replace the third tank 52 in the production of the flow 31 when the latter reaches its saturation point, while the second tank 51 remains isolated from said supply line 102 and is subjected to the regeneration phase, which originates the production of the flow 32.

In this way, in rotation, and similarly to what previously indicated, while the adsorbing means 1 of at least one tank, saturated during the previous adsorbing operations, are being regenerated, operation of the plant 100 and production of gases enriched in components (A) and (B) continue thanks to a second tank, with the further advantage that a third tank, in turn, participates in the production of gas flows 31 and 32 or also acts as a storage tank which in the first embodiment is constituted by the tank 55 dedicated exclusively to storage.

FIG. 2 schematically illustrates a method 200 for the separation of an initial gas mixture 101 containing a plurality of gaseous components, to be carried out in a plant 100 as previously described, comprising:

210: separating, by means of a first membrane-based separation stage 10, a flow of the gas mixture entering the plant 100, into a first flow of retentate gas 11, initially enriched in a first component (A) of said plurality of components, and into a first flow of permeate gas 12 initially enriched in a second component (B) of said plurality of components;

215: separating, by means of a second membrane-based gas separation stage 20, said first flow of retentate gas 11 into a final flow of retentate gas 21 further enriched in said first component (A) and into a second flow of permeate gas 22 suitable to be re-circulated in the plant 100 upstream of the first membrane-based gas separation stage 10, for example upstream of the compressor 42;

220: separating, by means of a third separation stage 30 with adsorption with oscillating pressure (PSA), said first flow of permeate gas 12 initially enriched in a second component (B) of said plurality of components, into a recirculable gas flow 31 suitable to be re-circulated in the plant upstream of said first membrane-based gas separation stage 10, for example upstream, or alternatively, if the pressure allows it, downstream of the blower 41, and into a final gas flow 32 further enriched in said second component (B).

In particular, as previously described with reference to the plant 100, the third gas separation stage 30 with adsorption with oscillating pressure (PSA), and in particular of the type at sub-atmospheric pressure (VSA or VPSA), comprises a plurality of separation tanks 50, 51, 52 and the step 220 of separating by means of the third stage comprises the phase 221 of switching in rotation among them the plurality of separation tanks when the plant is at steady state operations, so that:

at least a first tank 50 of said plurality of separation tanks is isolated from the supply line 102 of the first flow of permeate gas 12 and subjected to a regeneration phase of the adsorbing means 1 contained therein, by applying inside the first tank 50 a first pressure, preferably lower than the atmospheric pressure;

and at least one of the remaining separation tanks 51, 52 is connected to the supply line 102 and fed, at a second pressure higher than said first pressure, for example between 0.3 and 1 barg, with the flow of permeate gas 12 to be separated into said re-circulable gas flow 31 and into said final gas flow 32 further enriched in said second component (B).

In the case of the first embodiment of the third separation stage 30 shown in FIG. 3, i.e. where the third stage 30 comprises a first separation tank 50, a second separation tank 51, and a further storage tank 55 connected to the first and second separation tanks 50 and 51, the phase 221 of switching comprises the following steps:

222: storing in said storage tank 55 at least a part of the final gas flow 32 further enriched in said second component (B) outgoing from one or more of said first and second separation tanks 50 and 51;

224: re-introducing at least a part of the final gas flow 32, stored in the storage tank 55, into each of said first and second separation tanks 50, 51 for washing the adsorbing means 1 contained therein during the respective regeneration phase.

In practice, in this embodiment and as shown in the sequence in FIG. 3, once the plant is operating at steady state, for example while the second tank 51 is subjected to a regeneration phase and is on standby not connected to the supply line 102, the first flow of permeate gas 12 passes through the first tank 50 (Step 1) at a second pressure higher than the first pressure, with the adsorbing means 1 contained therein which adsorb in particular the component (B), for example carbon dioxide ($CO_2$), while the flows of re-circulable gas 31 are emitted and sent upstream of the blower 41 and here added to the flows of the gas mixture 101 which flow continually into the plant in order to be treated.

When the first tank 50 is being saturated, there is a brief transitory phase (Step 2) when both tanks 50 and 51 are connected to the supply line 102, then they move on to an operational situation (Step 3) when only the second tank 51 is connected to the supply line 102 and where the first flow of permeate gas 12 passes through with the adsorbing means 1 contained therein that adsorb in particular component (B), for example carbon dioxide ($CO_2$), while the flows of recirculable gas 31, still containing a significant percentage of component (A), for example methane, are emitted and sent upstream or downstream of the blower 41 and there added to the flows of gas mixture 101 which continually flow into the plant to be treated once again. Meanwhile, the first tank 50 begins the regeneration phase during which it is first connected to the storage tank 55, and the gas rich in component (B) contained therein, for example carbon dioxide ($CO_2$), is re-introduced into the first tank 50 for washing the adsorbing means 1 contained therein before carrying out the true regeneration process. The flow obtained in this phase contributes to the formation of the re-circulable flow 31 and is therefore recirculated for example upstream of the blower 41.

After washing, inside the first tank 50 a first pressure lower than the atmospheric pressure is applied, for example by means of connection to a vacuum pump 61 (Step 4); in this way, what entrapped in the adsorbing means is removed, and in particular the second component (B), for example carbon dioxide ($CO_2$), thus obtaining the final flow 32 further enriched in said second component. This flow 32 may contain a percentage of carbon dioxide ($CO_2$) even higher than 99% and which can be released for example into the atmosphere (off-gas), or reused for other purposes, for example alimentary purposes, and in part stored in the storage device 55.

Finally, in said situation (Step 5), the newly regenerated separation tank 50 is put on standby while waiting to be reconnected with the supply line 102, similarly to the situation described in Step 1 for the second tank 51.

When the latter reaches the saturation point, everything described above is repeated with the tanks reversed.

In the second embodiment of the third separation stage 30 shown in FIG. 4, i.e. where the third stage 30 comprises a first separation tank 50, a second separation tank 51, and a third separation tank 52, all totally similar and interchangeable among each other, the separation phase 220 comprises the sub-phase 221 of switching in rotation said first, second and third separation tanks, during operation of the plant, so that:

at least a first tank, for example tank 50, is isolated from the supply line 102 of the first flow of permeate gas 12 and subjected to a regeneration phase of the adsorbing means 1 contained therein, saturated with what previously adsorbed, by applying inside said first tank a first pressure, in particular lower than the atmospheric pressure;

a second tank, for example the second tank 51, is connected to the supply line 102 and fed at a second pressure higher than said first pressure with the first flow of permeate gas 12 to be separated;

and a third separation tank, for example the third tank 52, which has finished its regeneration phase, is at a pressure intermediate between that of the other two tanks, and is isolated from the supply line 102 of the first flow of permeate gas 12 while waiting to be reconnected to it.

In particular, in this embodiment, the switching sub-phase 221 comprises the following steps:

228: at a first instant, of so-called pre-saturation, in other words where the adsorbing means 1 contained in the separation tank 51 are close to saturation, connecting simultaneously the flow of permeate gas 12 to the third tank 52 and to the second tank 51 so that the gas flows which pass through the second tank are at least partially deviated also inside the third tank 52; and subsequently:

230: at a second instant, of so-called saturation, where the adsorbing means 1 contained in the second separation tank 51 reach saturation, disconnecting the second tank 51 from the supply line 102 and connecting it to the first tank 50, which in the meantime has finished the regeneration phase, in order to temporarily equalize between them the pressures inside the first tank 50 and the second tank 51 at a pressure level intermediate between the first pressure and the second pressure; and subsequently:

232: placing said regenerated first tank 50 and following the equalization of the pressures, in a position isolated from the supply line 102 of the first flow of permeate gas 12 and waiting to be reconnected thereto and, at the same time, subjecting said second tank 51 to a regeneration phase of the adsorbing means 1 contained therein saturated with what previously adsorbed, by applying inside said second tank 51 a first pressure, in particular lower than the atmospheric pressure.

In, practice, in this embodiment, when the plant is operating at steady state, a first tank 50 (STEP 10) is fed, by the supply line 102, with the first flow of permeate gas 12 at a higher pressure (second pressure or greater pressure) with its own adsorbing means 1 which adsorb in particular the component (B), for example carbon dioxide ($CO_2$), while the flows of re-circulable gas 31, still containing a considerable percentage of the component (A), for example methane, are emitted and sent upstream of the blower 41 and here added to the flows of gas mixture 101 which flow continually inside the plant in order to be treated. At the same time, the second tank 51, just regenerated and then brought to a pressure intermediate between that of regeneration and that of the supply line 102, is isolated from the supply line 102 and is on standby waiting to be reconnected thereto, while the third tank 52 is in the regeneration phase by applying inside a first pressure, i.e. a pressure lower than the atmospheric pressure, for example by means of connection to a vacuum pump 61.

In this way, all that is entrapped in the adsorbing means is removed and, in particular, the second component (B), for example carbon dioxide ($CO_2$), thus obtaining the final flow 32 further enriched in said second component, for example having a quantity of carbon dioxide ($CO_2$) even higher than 99% which, for example, can be released into the atmosphere (off-gas) or reused for other purposes, for example alimentary purposes.

Also in this case, when the first tank 50 is undergoing saturation, there is a brief transitory phase (STEP 11) where both the first and second tanks 50 and 51 are connected to the supply line 102, while the third regenerated tank 52 is on standby waiting for its turn to be reconnected to the line 102; then (STEP 12) an operational situation occurs when only the second tank 51 is connected to the supply line 102, where the first flow of permeate gas 12 flows through at a second pressure higher than the first pressure with the adsorbing means 1 therein contained which adsorb in particular the component (B), while the flows of recirculable gas 31 are emitted at the outlet.

During this time, the first tank 50 is connected to the third tank 52 on standby to equalize the pressures therein contained to an intermediate level between the first pressure of the third tank following regeneration and the high pressure inside the first tank 50 following the previous passing flow of permeate gas 12.

In this way, quantities of gas rich in the component (A), for example methane, are discharged into a tank which will subsequently go on-line, and which is partially pressurized while, advantageously, the tank to be regenerated is depressurized thus reducing consumption of the vacuum pump in the successive regeneration phase.

Once the pressures have been equalized, (STEP 13), the third tank 52 is isolated and on standby waiting for saturation of the second tank 51, while the first tank 50 is subjected to regeneration by applying inside it a first pressure lower than the atmospheric pressure, for example by means of connection to a vacuum pump 61; in this way, what entrapped in the adsorbing means 1 is removed, and in particular the second component (B), for example carbon dioxide ($CO_2$), thus obtaining again a final flow 32 further enriched in said second component.

In the successive stage (STEP 14), the first regenerated tank 50 is on standby waiting for its turn to be reconnected to said line 102, while there is a brief transitory phase when both the second tank 51 and the third tank 52 are connected to the supply line 102.

Subsequently (STEP 15), only the third tank 52 is connected to the supply line 102 and where the first flow of permeate gas 12 passes through at a second pressure higher than the first pressure with the adsorbing means 1 contained therein adsorbing in particular the component (B), while the flows of recirculable gas 31 are emitted at the outlet.

During this time, the second tank 51 is connected to the first tank 50 on standby, so as to equalize the pressures contained therein to a level intermediate between the first pressure inside the first tank following regeneration and the high pressure inside the second tank 51 following the previous passage of permeate gas 12.

Once the pressures have been equalized, (STEP 16), the first tank 50 remains isolated on standby waiting for saturation of the third tank 52, while the second tank 51 is subjected to regeneration by applying inside it a first pressure lower than the atmospheric pressure, for example by means of connection to a vacuum pump 61; in this way what is entrapped in the adsorbing means is removed and, in particular, the second component (B), for example carbon dioxide ($CO_2$), thus obtaining again a final flow 32 further enriched in said second component.

The procedure then continues with cyclic rotational switching of the tanks in the various operational situations, similarly to that previously described.

As can easily be understood by a person skilled in the art, the rotational switching of the tanks in the various operational situations previously described, may take place in moments or instants preferably predefined and pre-set, plant by plant, and/or said instants may also be calculated in real time and/or however redefined with respect to pre-set timing, during operation and on the basis of signals provided by suitable sensors associated for example to the tanks.

Similarly, in particular the moment or first instant when a tank is near saturation and the moment or second instant when saturation is considered reached, are preferably pre-defined and preset, application by application, in the control systems of a specific plant; and/or said first and second instants can be calculated in real time and/or recalculated and reset during operation on the basis of signals provided by suitable sensors associated for example to the tanks.

In practice, it has been evidenced how the plant 100 and the method 200 according to the disclosure make it possible to accomplish the scope as well as the objects prefixed. In particular, the use of a third separation stage with adsorption with variable or oscillating pressure, preferably of the vacuum pressure type, makes it possible to obtain adequate results in terms of desired purity of the gases selectively obtained from the initial biogas mixture, while utilizing a simplified constructive solution compared to solutions known in the art, which makes it possible to reduce the compression stages and, more generally, to reduce consumption and operational costs of the entire plant.

Naturally, without prejudice to the scope of the disclosure, many variations may be applied to the above-described exemplary and non-limiting embodiments and implementation details thereof, without departing from the spirit of the invention. For example, it is possible to modify the number of modules within the various separation stages and to use membranes of a different type; at least some stages of the method 200 may be carried out in a different sequence with respect to that described above for merely illustrative purposes, or all simultaneously; depending on the necessity and specific applications, it is possible to obtain final enriched gas flows with the desired percentage and degree of purity. For this purpose, the plant 100 can be suitably equipped with one or more regulation valves 60, appropriately controlled, for example by a plant control unit not illustrated in the drawings, so as to regulate the flow of gas entering and/or leaving the respective separation stages, for example by modifying the rate of flow, etc.

The invention claimed is:

1. A plant for the separation of a gas mixture containing a plurality of gaseous components, the plant comprising:
   a first membranes-based gas separation stage configured to receive a flow of said gas mixture in input and to separate the flow of said gas mixture into
      a first flow of retentate gas, initially enriched in a first component of said plurality of components, and
      a first flow of permeate gas, initially enriched in a second component of said plurality of components;
   a second membranes-based gas separation stage configured to receive said first flow of retentate gas in input and to separate the first flow of retentate gas into
      a final flow of retentate gas further enriched in said first component, and
      a second flow of permeate gas configured to be recirculated in the plant upstream of said first membranes-based gas separation stage;
   a third gas separation stage with adsorption with oscillating pressure, said third gas separation stage being configured to receive said first flow of permeate gas in input and to separate the first flow of permeate gas by adsorption into
      a recirculable gas flow configured to be recirculated in the plant upstream of said first membranes-based gas separation stage, and
      a final gas flow further enriched in said second component,
   wherein the third gas separation stage comprising a first separation tank, a second separation tank, and a third separation tank operatively connected to each other so that, during operation at a steady state of the plant, the first, second, and third separation tanks are switched in rotation among the first, second, and third separation tanks such that:
      at least said first separation tank is isolated from a supply line of the first flow of permeate gas and is subjected to a regeneration phase of adsorption contained therein by applying a first pressure inside the first tank,
      said second tank is connected with the supply line and fed, at a second pressure higher than said first pressure, with said first flow of permeate gas to be separated, and
      said third separation tank finishes a regeneration phase of an adsorbing system contained therein and is brought to an intermediate pressure between the first pressure of the first separation tank and the second pressure of the second separation tank and is isolated from the supply line of the first flow of permeate gas and waiting to be reconnected thereto, wherein reconnection of said third separation tank to the supply line of the first flow of permeate gas takes place when the adsorbing system contained in the second tank reaches the saturation level by simultaneously connecting the supply line of the first flow of permeate gas to the third separation tank and to the second separation tank so that the first flow of permeate gas which passes through the second separation tank is at least partially deviated inside the third separation tank.

2. A method for the separation of a gas mixture containing a plurality of gaseous components, the method comprising:
separating, by a first membranes-based gas separation stage, a flow of the gas mixture entering a plant, into
a first flow of retentate gas, initially enriched in a first component of said plurality of components, and
a first flow of permeate gas initially enriched in a second component of said plurality of components;
separating, by a second membranes-based gas separation stage, said first flow of retentate gas into
a final flow of retentate gas further enriched in said first component, and
a second flow of permeate gas configured to be recirculated in the plant upstream of the first membranes-based gas separation stage;
separating, by a third gas separation stage with adsorption with oscillating pressure, said first flow of permeate gas initially enriched in a second component of said plurality of components into
a recirculable gas flow configured to be recirculated in the plant upstream of said first membranes-based gas separation stage, and
a final gas flow further enriched in said second component,
wherein the third gas separation stage comprises a first separation tank, a second separation tank, and a third separation tank operatively connected to each other, and
the separating by the third gas separation stage comprises switching the first, second, and third separation tanks, during operation of the plant, in rotation among the first, second, and third separation tanks such that:
said first separation tank is isolated from a supply line of the first flow of permeate gas and subjected to a regeneration phase of an adsorbing system contained therein by applying a first pressure inside the first tank,
said second tank is connected to the supply line of the first flow of permeate gas and fed the first flow of permeate gas at a second pressure higher than said first pressure, with said first flow of permeate gas to be separated,
said third separation tank finishes a regeneration phase of an adsorbing system contained therein and remains isolated from the supply line of the first permeate gas flow waiting to be reconnected thereto, and
at a first instant, at which an absorbing system contained in the second separation tank is close to saturation, connecting the flow of permeate gas simultaneously to the third separation tank and to the second separation tank so that the first flow of permeate gas that passes through the second separation tank is at least partially deviated inside the third separation tank.

3. The method according to claim 2, further comprising:
at a second instant, at which the adsorbing system contained in the second separation tank reaches saturation, disconnecting the second separation tank from the supply line and connecting the second separation tank to the regenerated first separation tank in order to temporarily equalize between the regenerated first tank and the second separation tank the pressures inside the first separation tank and inside the second separation tank at a pressure level intermediate between the first pressure and the second pressure; and
subsequently, following pressure equalization, placing said regenerated first tank in a position isolated from the supply line of the first flow of permeate gas and waiting to be reconnected thereto, and at the same time, subjecting said second separation tank to the regeneration phase of the absorbing system contained therein saturated by previous absorption, by applying the first pressure inside said second separation tank.

4. The plant according to claim 1, further comprising a vacuum pump, and
wherein said first tank is subjected to said regeneration phase of the adsorbing system contained therein at said first pressure lower than the atmospheric pressure by operating said vacuum pump.

5. The plant according to claim 1, wherein said first component of said plurality of components is methane.

6. The plant according to claim 1, wherein said second component of said plurality of components is carbon dioxide.

7. The plant according to claim 1, wherein said second tank is connected with the supply line and fed with said first flow of permeate gas to be separated, at a second pressure comprised between 0.3 and 1 barg.

8. The method according to claim 2, wherein said first tank is isolated from a supply line of the first flow of permeate gas and subjected to a regeneration phase of the adsorbing system contained therein by applying, inside the first tank, and by a vacuum pump, a first pressure lower than the atmospheric pressure.

9. The method according to claim 2, wherein said first component of said plurality of components is methane.

10. The method according to claim 2, wherein said second component of said plurality of components is carbon dioxide.

11. The method according to claim 2, wherein said second separation tank is connected with the supply line and fed with said first flow of permeate gas to be separated, at a second pressure comprised between 0.3 and 1 barg.

* * * * *